United States Patent [19]

Mazumder et al.

[11] Patent Number: 4,633,714

[45] Date of Patent: Jan. 6, 1987

[54] AEROSOL PARTICLE CHARGE AND SIZE ANALYZER

[75] Inventors: Malay K. Mazumder, Little Rock; Ron E. Ware, Sheridan, both of Ark.

[73] Assignee: University of Arkansas, Little Rock, Ark.

[21] Appl. No.: 765,144

[22] Filed: Aug. 13, 1985

[51] Int. Cl.$^4$ ............................................. G01N 29/00
[52] U.S. Cl. ........................................ 73/596; 73/643; 73/865.5; 356/336
[58] Field of Search ................... 73/596, 643, 432 PS, 73/432 L; 356/336; 364/555

[56] References Cited

U.S. PATENT DOCUMENTS 3,208,286  9/1965  Richard ........................... 73/432 PS
3,763,428 10/1973  Preist ............................... 73/432 PS

OTHER PUBLICATIONS

J. Masters, "An Aerosol Analyzer" 24 Review of Scientific Instruments 586–588 (Aug. 1953).
W. Megaw and A. Wells, "Electrical Mobility of Submicron Particles", 219 Nature 259–261 (Jul. 20, 1968).
M. Mazumder, R. Ware, and W. Hood, "Simultaneous Measurements of Aerodynamic Diameter and Electrostatic Charge on a Single-Particle Basis", Chapter 11 of Measurement of Suspended Particles by Quasi-Elastic Light Scattering, 327–341 (edited by B. Dahneke), Wiley-Interscience, New York (1983).
M. Mazumder et al., "Real-Time Measurements and Control of Particle Charge as Applied to Electrostatically Enhanced Fabric Filters", University of Arkansas Graduate Institute of Technology Technical Progress Report, No. UCRL-15582 S/C 6166601, dated Aug. 1983.
W. Bergman et al., "Electric Air Filtration: Theory, Laboratory Studies, Hardware Development, and Field Evaluations" Lawrence Livermore Laboratory Report, I.D. No. UCID-19952 (Sep. 1983).

Primary Examiner—Anthony V. Ciarlante
Attorney, Agent, or Firm—Hill, Van Santen, Steadman & Simpson

[57] ABSTRACT

An instrument for analyzing the size and charge of aerosol particles employs a dual beam laser Doppler velocimeter to track the motion of a particle while subjecting the particle to a sinusoidal acoustic field and to a pulsed, high voltage electric field. The particle transmitting through the crossed beams of the laser Doppler velocimeter moves with an oscillatory motion due to the acoustic field and, if the particle is charged, it has a horizontal drift parallel to the electric field during the electric pulse. The phase lag of the particle's motion with respect to the acoustic field is measured to determine the aerodynamic diameter of the particle and the velocity and the direction of the drift relative to the polarity of the applied high voltage electric field is used to determine the magnitude and polarity of the electric charge of the particle.

18 Claims, 19 Drawing Figures

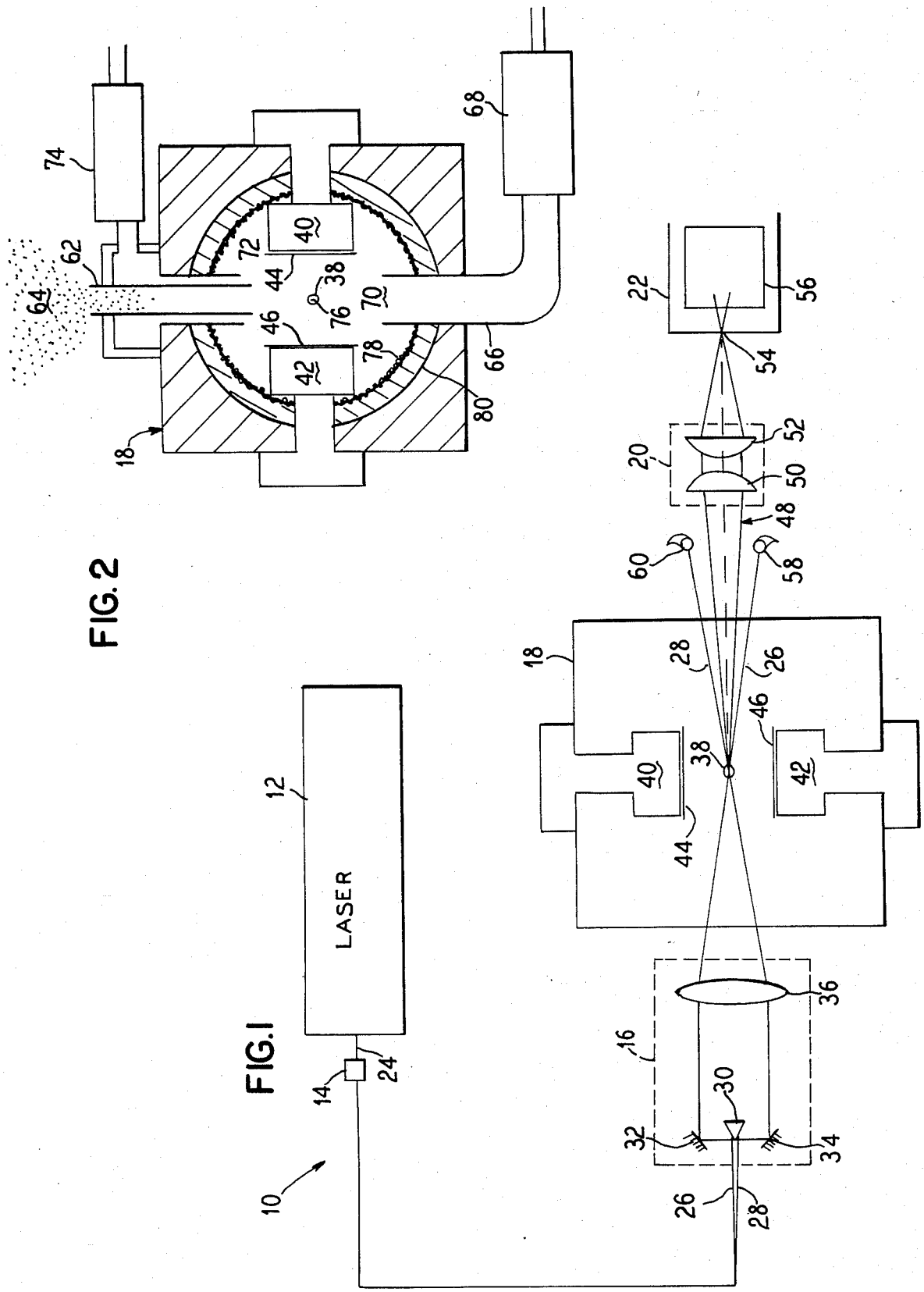

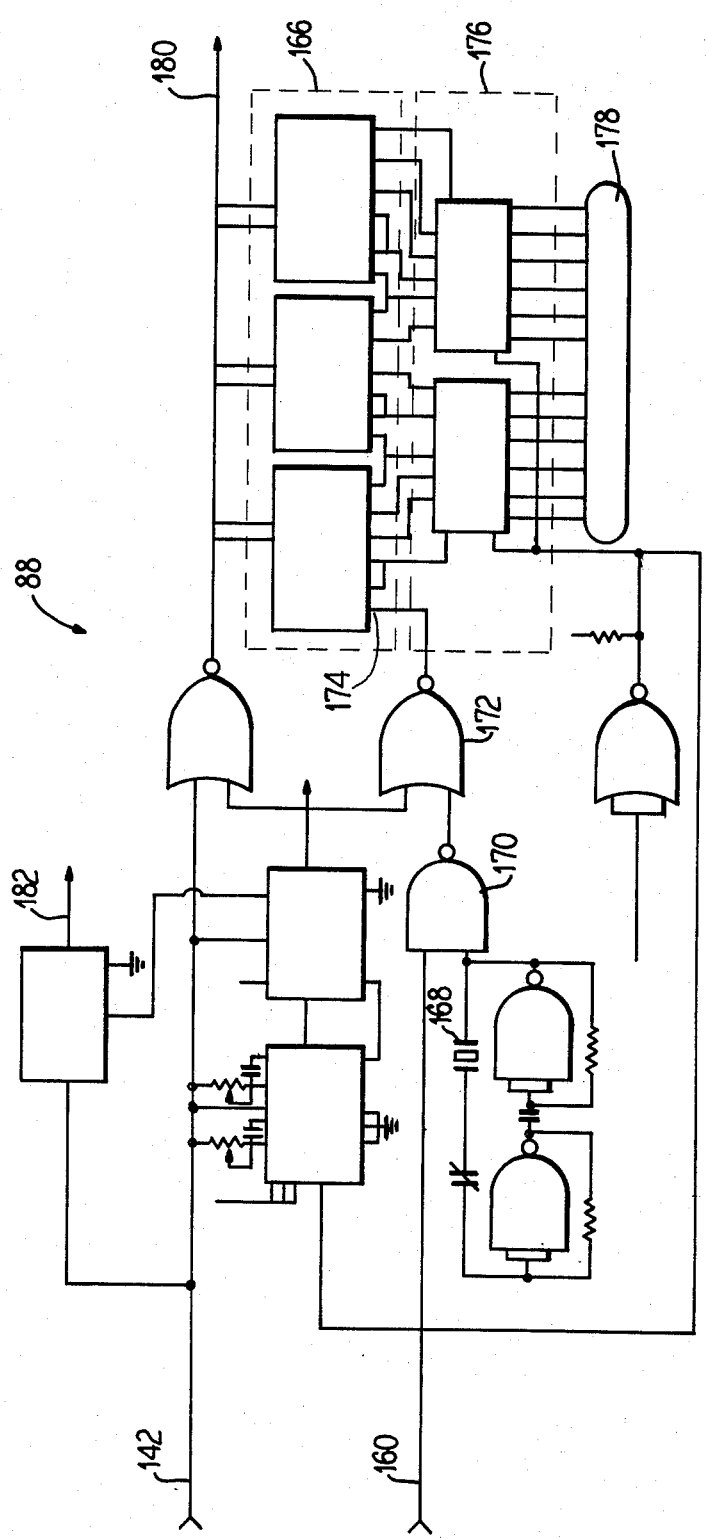

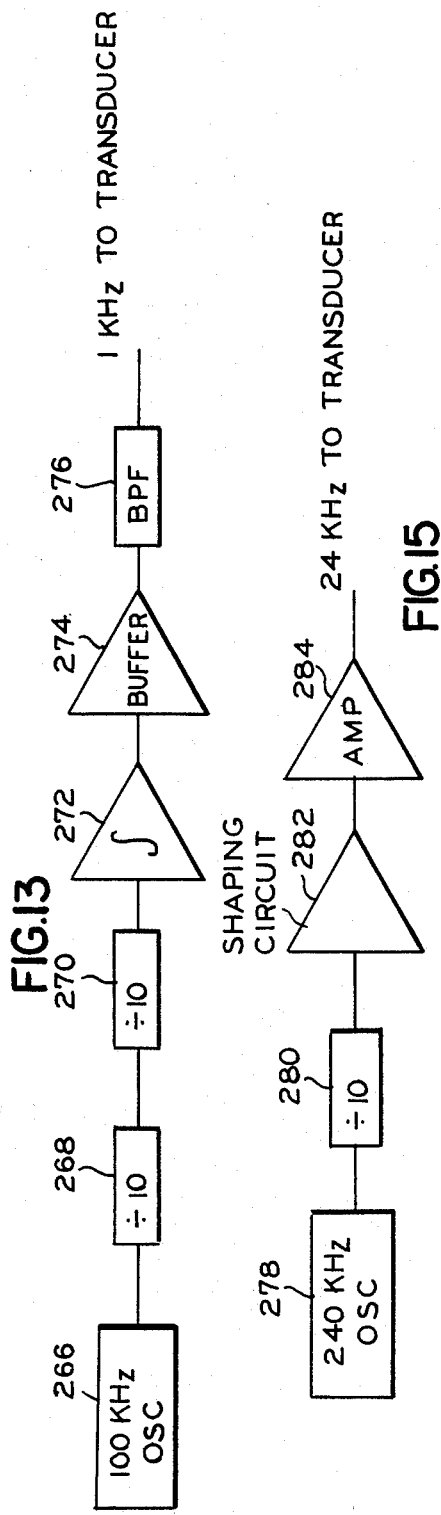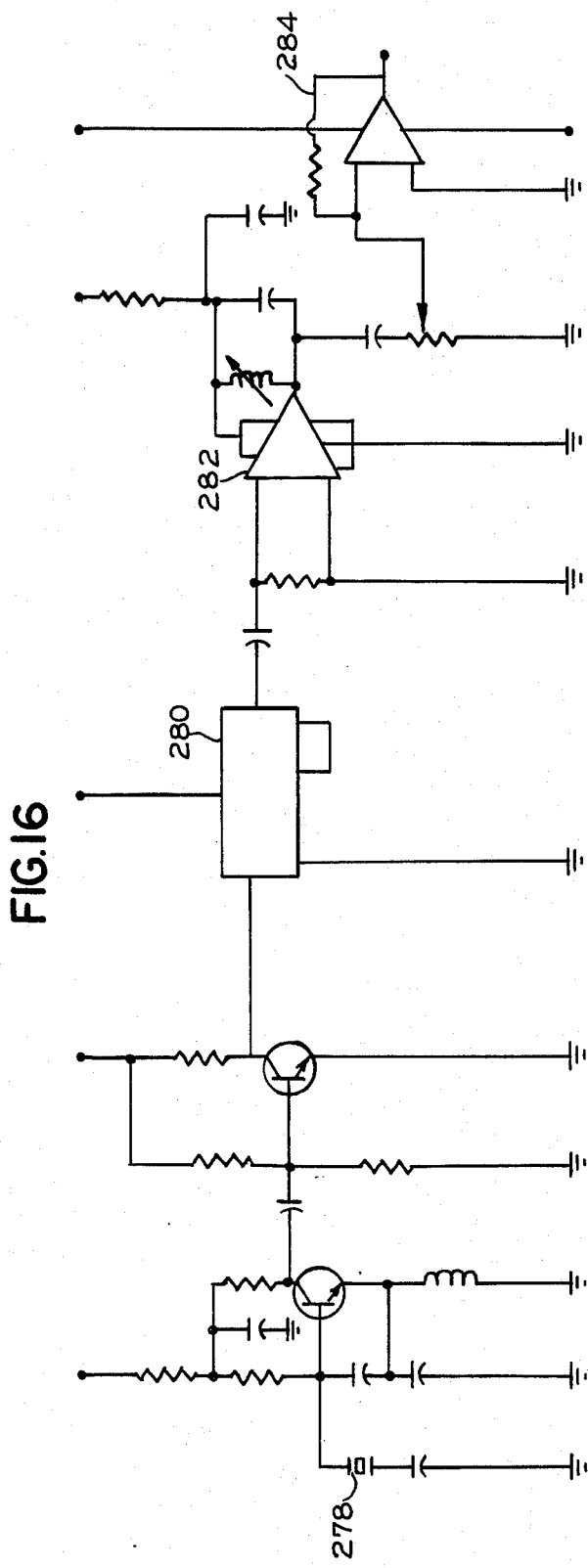

AEROSOL PARTICLE CHARGE AND SIZE ANALYZER

BACKGROUND OF THE INVENTION

1. Field of the Invention

The present invention relates generally to a device for measuring the aerodynamic size and electrical charge of airborne particles and in particular, to a device that subjects aerosols to an acoustic field and to an electric field and thereafter senses the motion of individual airborne particles through the use of a laser Doppler velocimeter.

2. Description of the Prior Art

Measurement of the charge and size of aerosol particles has been sought using a variety of different devices. For instance, an article entitled "An Aerosol Analyzer" by Joseph I. Masters, 24 Review of Scientific Instruments 586 (August 1953), describes a device for collecting charged aerosol particles on filter paper and thereafter measuring the average charge of the particles collected. The charge distribution of the particles cannot be determined, however, nor can the presence of bipolar charges.

An article entitled "Electrical Mobility of Submicron Particles" by W. J. Megaw et al, 219 Nature 259 (July 20, 1968), describes a device for accumulating deposits in a copper foil lined box through which a radioactive aerosol is passed so that the electrical mobility of the sample can be determined. Filtered air is passed in around the aerosol inlet so that it is possible to adjust the thickness of the flow stream.

Lewis et al U.S. Pat. No. 4,375,673 discloses a charge spectrograph wherein a uniform electric field is applied to charged toner particles by a series of rectangular electrodes and the particles collected on filter paper so that the average size and charge can be found from the deflections of the particles.

Mazumder et al, "Simultaneous Measurements of Aerodynamic Diameter and Electrostatic Charge on a Single Particle Basis" in Measurement of Suspended Particles by Quasi-Elastic Light Scattering 327 (B. Dahneke ed. 1983) discloses a method for analyzing aerosol particles wherein an oscillating electric field is applied to the particle and its size and charge are determined from the phase lag of the particle as compared to the electric field. The device uses a laser Doppler velocimeter to detect the particles' motion. However, uncharged particles are not detectable by this device.

Additional prior art includes: Millikan, R. A. (1909). 79th Meeting of the Br. Assoc. Adv. Sci., Winnepeg, Manitoba; T. Gillespie, et. al., "An Instrument for Determining the Electric Charge Distribution in Aerosols," 30 Canadian Jour. of Chemistry 1056 (Dec. 1952); U.S. Pat. Nos. 2,537,628, Hanson et. al.; 3,208,286, Richard; 3,723,712, Komline, Sr. et. al.; and 3,944,797, Coulter et. al.

SUMMARY OF THE INVENTION

In order to make rapid simultaneous measurements of the aerodynamic size and electrical charge of individual particles in an aerosol in real time and to provide analysis of the distributions of the size and charge of the particles in an aerosol sample even though it is necessary to accommodate various size ranges of particles, an aerosol particle charge and size analyzer and method is provided in which a dual-beam laser Doppler velocimeter (LDV) detects the motion of a particle while the particle is subjected to an acoustic field and an electrical field simultaneously. Individual particles of an aerosol move through the crossed beams of the LDV with an oscillitory motion due to the acoustic field and, additionally if the particle is charged, a horizontal drift parallel to the superimposed electric field. The phase lag and/or the amplitude, of the particle's motion with respect to the acoustic field is measured to determine the aerodynamic diameter of the particle. A measure of the velocity and the direction of the drift with respect to the electrical field can then be used to determine the magnitude and polarity of the electrical charge of the particle.

The device of the present invention measures aerosol particles moving in a flow stream and, through the application of an electro-acoustic field to the particles, provides quick and accurate analysis so that in-situ measurements can be made in real time.

The use of an acoustic field generated by an acoustic transducer enables both charged and uncharged particles to be measured, and, in a preferred embodiment, the use of high voltage pulsed electrical signals which are reversed in alternating pulses minimizes particle precipitation. A variety of electrode shapes may be used to generate the electric field, although disk-shaped electrodes mounted on the acoustic transducer are preferred to provide uniform electrical fields aligned with the acoustic field.

Several operating parameters of the present device are variable to accommodate various size particles, including varying the angle of intersection between the two laser beams of the LDV to permit the measurement of particle sizes within a wide range. A sheath of clean air flow controls the residence time of particles within the crossed beams of the LDV for improved accuracy.

The present device also includes signal processing circuitry for use with a program controlled microprocessor which demodulates the LDV signal to derive the particle motion caused by acoustic excitation so that the phase lag of the particle motion and/or the amplitude difference of the particle motion with respect to the acoustic excitation can be determined. The electrical circuitry also is capable of distinguishing the particle motion component due to acoustic excitation from the component due to the applied electrical field.

Data processing circuitry, in conjunction with software programs, are capable of storing and displaying the aerodynamic size distribution and the electrostatic charge distribution of an aerosol sample so that the distributions can be plotted. The present device is also capable of providing and plotting the distribution of the electrical mobility of individual particles as well as the concentration of the aerosol sample.

The device of the present invention may be used in quality control of aerosol generation processes, evaluation of electrostatic fabric filters and electrostatic precipitators, measurement of charge-to-mass ratio of powders, especially toner particles used in electrophotography, and characterization of electrostatically charged fog used for fugitive dust control. The electrostatic charge of inhaled aerosol particles may affect the retention of particles inside the lung. Therefore, in aerosol therapy, an analysis of the electrostatic charge of medical aerosol particles can have possible use in enhancing lung deposition. Other applications are contemplated as well.

BRIEF DESCRIPTION OF THE DRAWINGS

FIG. 1 is a schematic diagram of an aerosol particle charge and size analyzer according to the principles of the present invention.

FIG. 2 is a cross-section of the relaxation chamber of the analyzer shown in FIG. 1.

FIG. 9 is an electrical diagram of the size counter of FIG. 5.

FIG. 13 is a functional block diagram of an acoustic transducer drive circuit for use in the embodiment shown in FIG. 11.

FIG. 15 is a functional block diagram of an acoustic transducer drive for use with the embodiment shown in FIG. 12.

FIG. 16 is an electrical circuit diagram of the acoustic drive shown in FIG. 15.

DESCRIPTION OF THE PREFERRED EMBODIMENTS

Figure 3:
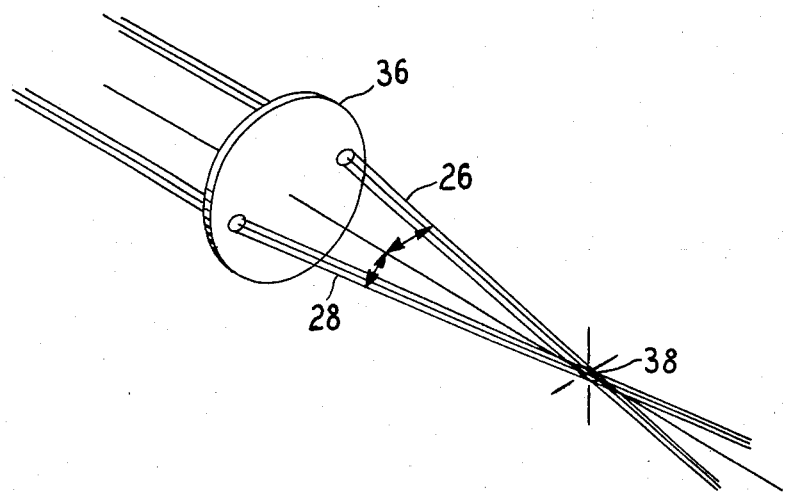
FIG. 3 is a perspective view showing the intersection of two light beams from FIG. 1 to form a sensing volume.
Figure 4:
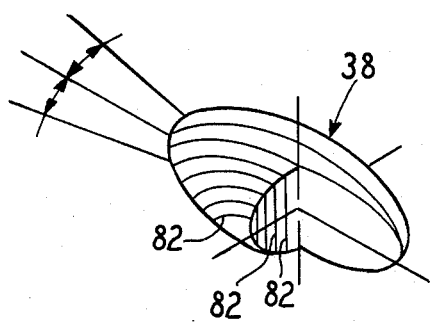
FIG. 4 is an enlarged perspective view of the sensing volume of FIG. 3, shown partially cut-away.

An aerosol particle charge and size analyzer is shown in FIG. 1 generally at 10. The device includes a laser 12, an acousto-optic modulator 14, a beam focusing apparatus 16, a relaxation chamber 18, a scattered light focusing apparatus 20, and a photodetector device 22. More specifically, the laser 12 generates a monochromatic light beam 24, which is preferably polarized. The laser beam 24 is passed through an acousto-optic modulator, or Bragg cell 14, which produces several diverging light beams each coherent with the other beams but differing in optical frequency. Two of the diverging light beams 26 and 28 are separated using a mirrored prism 30. The other diverging light beams are not used and, therefore, are removed such as by an aperture or beam stops (not shown). The two light beams 26 and 28 are preferably of approximately equal intensities.

Mirrors 32 and 34 in conjunction with lens 36 are used to focus the two beams 26 and 28 so that they cross within the relaxation chamber 18. As the beams 26 and 28 cross, they form a measuring volume 38 through which particles pass for measurement. The measuring volume 38 is located between first and second acoustic transducers 40 and 42 each of which have an electrode 44 and 46, respectively, mounted thereon over the faces of the transducers 40 and 42.

As particles pass through the measuring volume 38 they scatter the light from the beams 26 and 28. The scattered light, indicated generally at 48, is focused by lenses 50 and 52 through an aperture 54 in the photodetector device 22. A photomultiplier 56 is used to detect the scattered light 48.

The unscattered light from beams 26 and 28, after passing through the measuring volume 38 is no longer needed and, thus, is blocked by beam stops 58 and 60, respectively.

A laser 12 which has been used in the present device is a Spectra Physics Argon ion laser Model 164-06 which has been tuned to operate in a single frequency mode at a wavelength of 0.514 microns. The beam is vertically polarized upon leaving the laser housing. Helium-Neon lasers are less expensive and more portable and may be used in lieu of Argon ion lasers.

The light beam 24 is fed into a Crystal Technology Acousto-optic modulator Model 3110 which produces light beams shifted in frequency by 40 MHz.

The Relaxation Chamber

FIG. 2 shows the relaxation chamber 18 in more detail. The relaxation chamber 18 includes an inlet tube 62 through which aerosol particles 64 are drawn and an outlet tube 66 connected to a controlled vacuum system 68 which creates a slight negative pressure in the interior 70 of the chamber 18. The negative pressure causes the aerosol particles 64 to be drawn into the chamber interior 70.

An aerosol flow stream is established by the inlet tube 62 which is mounted concentrically within a sheath air tube 72 through which a sheath of clean air is fed after being filtered by particle filter 74. The sheath airflow rate is controlled by using a positive pressure air flow source (not shown) to control the residence time of individual particles 76 within the measuring volume 38. The light beams 26 and 28 which form the measuring volume 38 are admitted into the relaxation chamber 18 through windows (not shown).

The acoustic transducer 40 generates standing wave acoustic field within the chamber 18 perpendicular to the direction of flow of the sample aerosol 64. Acoustic absorbing material 78 is mounted on the interior walls 80 of the chamber 18 to reduce reflections from the walls 80, which are preferably of metal. The gas in which the aerosol particles 64 are suspended is moved sinusoidally within the chamber 18 by the acoustic field. A second, passive acoustic transducer 42 is used to monitor the acoustic field. It is alos foreseen to monitor the driving signals of the active transducer 40 to determine the acoustic field, although this is a less accurate way of determining the motion of the gas.

Viscous forces cause the particles of the aerosol 64 to attempt to follow the motion of the gas. Due to the inertia of the particles, their motion lags behind that of the gas and has a lower amplitude. The phase lag and the relative amplitude reduction of a particle's motion with respect to the gas are functions of the aerodynamic diameter of the particle for various frequencies of the acoustic field. A measure of either the phase or the amplitude (displacement or velocity) of a particle's motion relative to that of the surrounding gas can be used directly to calculate the aerodynamic diameter of the particle. Equations for this calculation are as follows:

$$\frac{V_p}{U_g} = \frac{1}{\sqrt{1 + \omega^2 \tau^2}}, \text{ and} \quad (1)$$

$$\phi = \tan^{-1} \omega \tau_p \quad (2)$$

where
$V_p$ is the peak velocity of the particle,
$U_g$ is the peak velocity of the gas,
$\omega$ is the angular acoustic frequency,
$\phi$ is the relative phase difference between the motion of the particle and the motion of the gas.
$\tau_p$ is known as the "relaxation time" of the particle and is given by:

$$\tau_p = \frac{\rho_a d_a^2 C_c(da)}{18\eta}, \quad (3)$$

where $\rho_a = 1$ g/cm², $d_a$ is the aerodynamic diameter of the particle, $\eta$ is the viscosity of the gas, and $C_c$ is the Cunningham slip correction factor, a semi-empirical valve required where the particle size is not much greater than the mean free path of the gas molecules.

The aerosol is also subjected to a pulse of high voltage electric field generated by the electrodes 44 and 46. At least one of the electrodes 44 and 46 may be spherical to avoid corona discharge resulting from the high voltage, which may be up to several thousand volts. The electrodes 44 and 46 consist either of a thin foil or a fine wire mesh placed over the face of the transducers 40 and 42. The corona discharge is eliminated by providing insulating rims at the edges of disc-shaped electrodes, which results in a more uniform electric field within the measuring volume 38.

The maximum velocity reached by a particle having an electrical charge q in an electrical field of strength $E_s$ is given by:

$$V_E = \frac{qC_cE_s}{3\pi\eta d_a}, \quad (4)$$

where $C_c$, $\eta$, and $d_a$ are as previously defined.

A particle's motion transverse to the flow direction is a superposition of a unidirectional drift due to the applied electric field during the duration of the pulse and an oscillatory motion due to the acoustic field. A measure of the drift velocity $V_E$ due to the electric field can, hence, be used to calculate the charge, q, on the particle, provided the electric field strength $E_s$ is known, and the aerodynamic diameter $d_a$ of the particle is determined from the particle's motion due to the acoustic field.

A DC pulse is applied to the electrodes 44 and 46 to generate the electric field. Each subsequent pulse may have the same polarity as the preceding pulse. However, this has been found to cause precipitation of the particles and, therefore, in a preferred embodiment the polarity of each subsequent pulse is reversed.

Laser Doppler Velocimeter

The measuring volume 38 is defined by the region of intersection of the two laser beams 26 and 28, as can be seen in FIG. 3. The interference of the electro-magnetic waves of the two beams 26 and 28 creates a pattern of parallel light and dark planes 82 in the measuring volume 38. As a particle moves through the measuring volume 38, the intensity of light scattered from the particle depends on its position relative to the bright and dark planes 82. The planes 82 bisect the angle of intersection of the light beams 26 and 28 and, thus, are aligned parallel to the direction of flow of the aerosol through the chamber 18 and perpendicular to the electric and acoustic fields. Hence, motion of a particle caused by these fields causes variations in the intensity of the light scattered by it but motion of the particle in the flow stream does not. Proper alignment of the beams 26 and 28 with respect to one another, since improper alignment would cause a portion of the flow motion to appear as a charge component.

The defracted beam 28 from the acousto-optic modulator 14 is shifted in frequency from the undefracted beam 26. This results in a unidirectional motion of the bright and dark planes 82 at the modulation frequency $f_o$ of the modulator 14. Hence, the optical signal at the photodetector 56 due to light scattered from the particle has a frequency $f_s$ given by:

$$f_s = f_o + f_E + f_{ao} \sin(2\pi f_a t) \quad (5)$$

where
$f_E = V_E/d_f$ is the drift frequency due to the electric field,
$f_{ao} = V_p/d_f$ is the maximum signal frequency change due to the acoustic drive,
$f_a$ = the acoustic drive frequency.
$d_f$ is the spacing between the bright lines of the laser beam interference pattern in the measuring volume 38 and is given by:

$$d_f = \frac{\lambda}{2 \sin \phi/2}, \quad (6)$$

where $\phi$ is the crossing angle of the laser beams 26 and 28 at the measuring volume 38 and $\lambda$ is the optical wavelength of the laser light. The intensity of the light in the laser beams 26 and 28 has a Gaussian profile, rather than being uniform, therefore the intensity of light within the measuring volume also has a Gaussian profile.

The sinusoidal portion of this signal is isolated from the carrier frequency ($f_o + f_E$) by electronic frequency demodulation techniques. The phase, or amplitude, of the sinusoidal portion has been compared in a microprocessor to that known for a size calibration particle and then to a precalculated look-up table so that an aerodynamic diameter can be assigned to the particle.

The frequency $f_E$ due to the electric field acting on a charged particle is found by measuring the average period $T_s$ of cycles of the Doppler signal occurring an integral number of acoustic cycles and comparing this measurement to the carrier period $1/f_o$. Thus $F_E$ is given by:

$$f_E = (1/T_s) - f_o.$$

The drift velocity is given by $V_E = d_f f_E$ and the charge q on the particle is then determined from equation (4). The measurement is performed only when the applied field electric attains a quasi-steady value and the particle attains the quasi-steady migration, or drift, velocity. The polarity of the electrical field is reversed during each subsequent pulse in the preferred embodiment and, as a result, the precipitation loss is minimized.

Signal Processing

Figure 5:
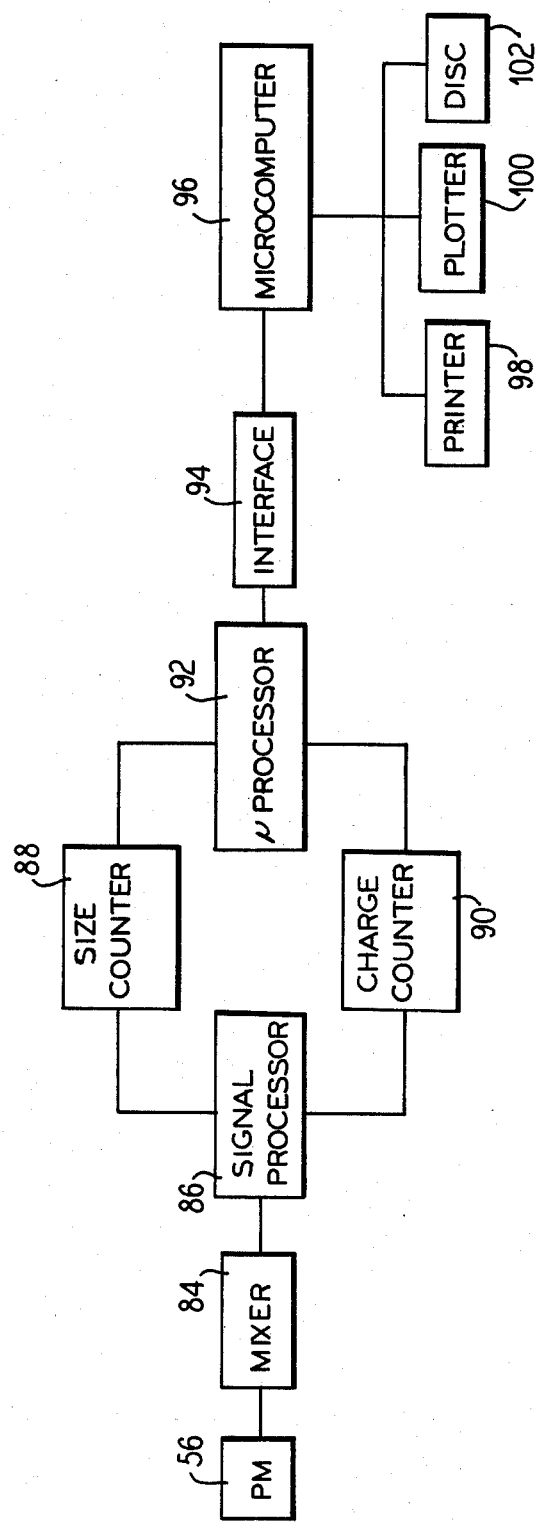
FIG. 5 is a functional block diagram of signal processing circuitry according to the principles of the present invention for use with the analyzer of FIG. 1.

A single charged aerosol particle, traversing the measuring volume 38 and being driven by the acoustic and electric fields, produces an FM signal burst at the output of the photomultiplier tube 56. The FM carrier frequency is the LDV bias frequency plus the frequency associated with the electrical mobility of the particle and the modulation side bands are produced by sinusoidal particle motion. As shown in FIG. 5, the current produced at the output of the photomultiplier tube 56, is fed into a mixer 84, and is heterodyned, or mixed, to produce a two MHz FM signal burst for further processing.

The FM signal is demodulated by a phase-locked loop based signal processor 86. The output of the signal processor 86, which represents the instantaneous velocity of an aerosol particle, is passed through a bandpass filter and then converted into a pulse train by a high speed comparator (see FIG. 7). The signal is then applied to a size counter 88 and to a charge counter 90. The output signals from the size counter 88 and the charge counter 90 are fed into a microprocessor 92, which computes both the size and charge for each particle. The size and charge information for each particle is stored by the microprocessor 92. Once the desired amount of data is collected, the size and/or the charge distribution of the tested aerosol can be plotted by using an interface 94 which connects the microprocessor 92 to a microcomputer 96, such as a desk top microcomputer, that may optionally include a printer 98 a plotter 100 and a disk drive 102. An example of a photomultiplier tube 56 for use with the present device is a Hamamatsu side-on type photomultiplier tube, model R928.

Figure 6:
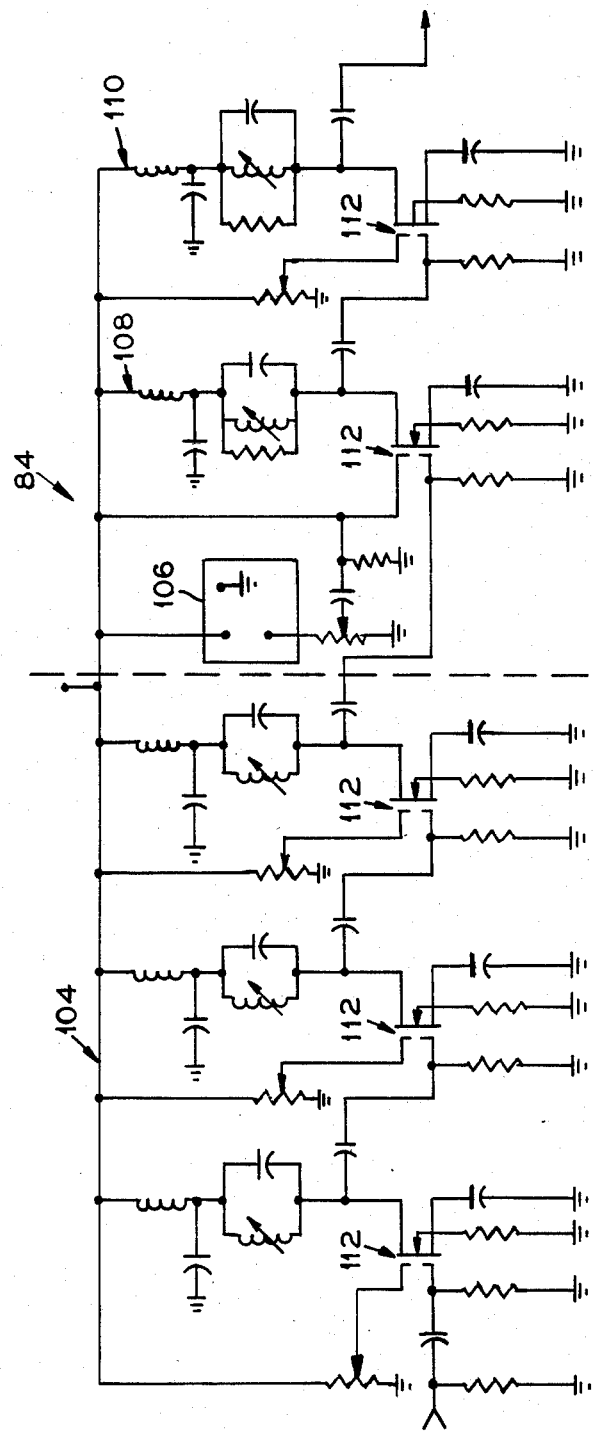
FIG. 6 is an electrical circuit diagram showing the mixer of FIG. 5.

FIG. 6 shows the mixer 84 which converts the 41 MHz laser Doppler burst recovered from the photomultiplier tube 56 to a 2 MHz IF frequency. The mixer 82 consists of a three stage tuned amplifier portion 104, a 39 MHz local oscillator 106, a mixer stage 108 and a buffer 110. Each stage of the amplifier 104, as well as the mixer stage 108 and buffer 110, consists of a dual-gate insulated-gate field-effect transistor (IGFET) 112, model 3N187, and its biasing circuitry.

Figure 7:
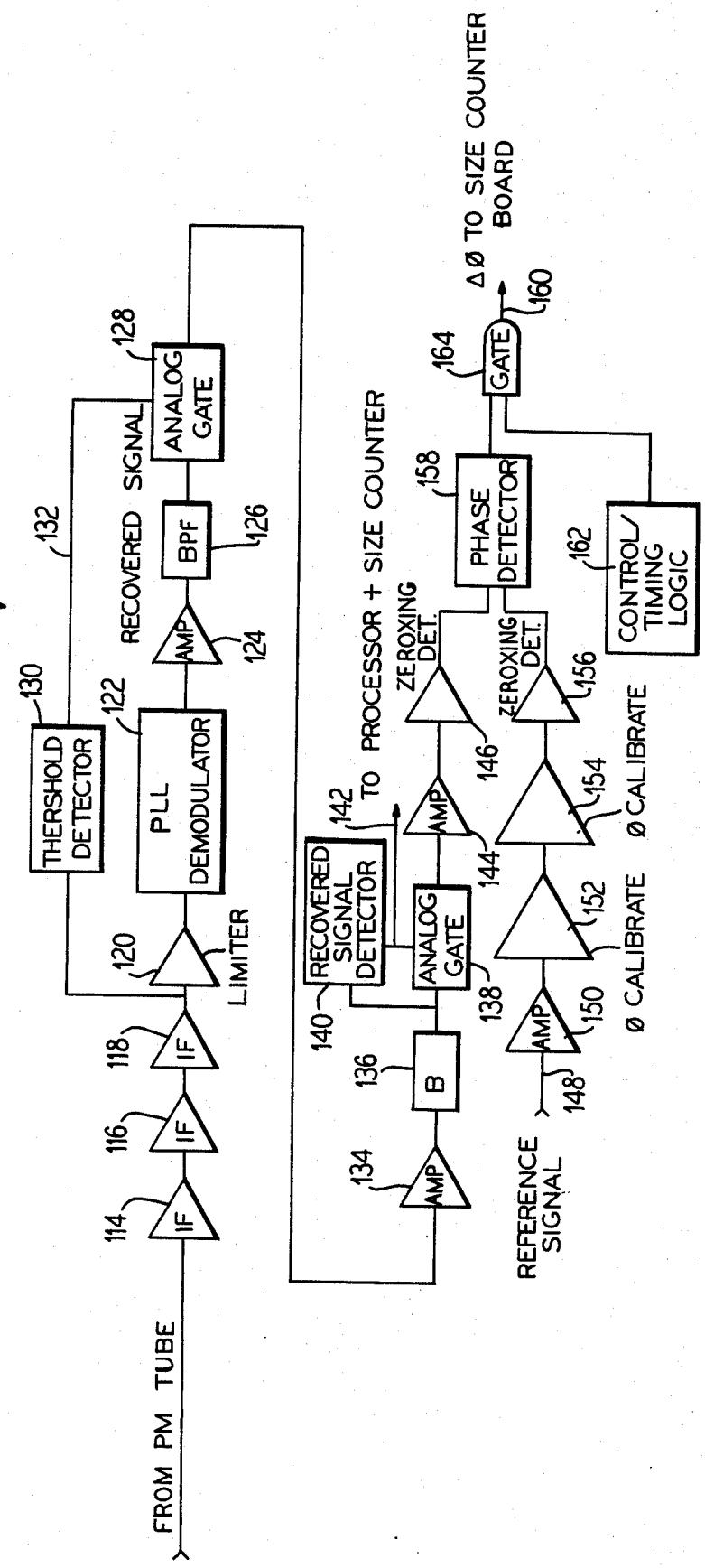
FIG. 7 is a functional block diagram showing the signal processor of FIG. 5.

FIG. 7 shows the signal processor 86 which receives the two MHz signal from the mixer 84 and demodulates it to eliminate the 2 MHz carrier. The signal processor circuit includes the following: a three stage tuned amplifier 114, 116, and 118, a limiter 120 and a phase locked loop 122. The output of the phase locked loop represents the instantaneous velocity of the particle and is fed through an amplifier 124, a band pass filter 126, and then to an analog gate 128.

An RF threshold level detector 130 determines whether the output signal of the amplifier stage 118 exceeds a predetermined threshold level, and, if so, triggers the analog gate 128 through lead 132 to allow the signal processing sequence to continue is in a loop 132 which also feeds the analog gate 124. If the amplitude of the RF signal from amplifier 118 is greater than the selected level, the particle velocity, or recovered, signal is gated through the analog gate 128 to an amplifier 134 and a band pass filter 136. In this manner low level, unwanted signals are rejected.

The second amplifier 134 and the band pass filter 136 are followed by a second analog gate 138 and by a recovered signal detector 140. If the velocity, or recovered, signal is of sufficient amplitude, it is gated through the analog gate 138 to a buffer 144 and a zero crossing detector 146, where the sinusoidal signal is changed to a pulse train of 5 volt square waves.

A reference signal, which is received at an input 148 from the acoustic transducer 42, is amplified by amplifier 150 and then passed through a two-stage phase shifting circuit 152 and 154. A zero crossing detector 156 converts the reference signal into a 5 volt square wave pulse train, similar to that of the recovered signal. The reference pulse train and the recovered pulse train are then fed to a phase detector 158, in the form of an exclusive OR gate. The resulting output is a square wave whose frequency is twice that of the reference signal or the recovered signal. The pulse width of this square wave is the phase difference between the recovered signal and the reference signal. The phase difference signal is gated to the size counter 88 at lead 160 by a control timing logic unit 162 through gate 164.

Figure 8A:
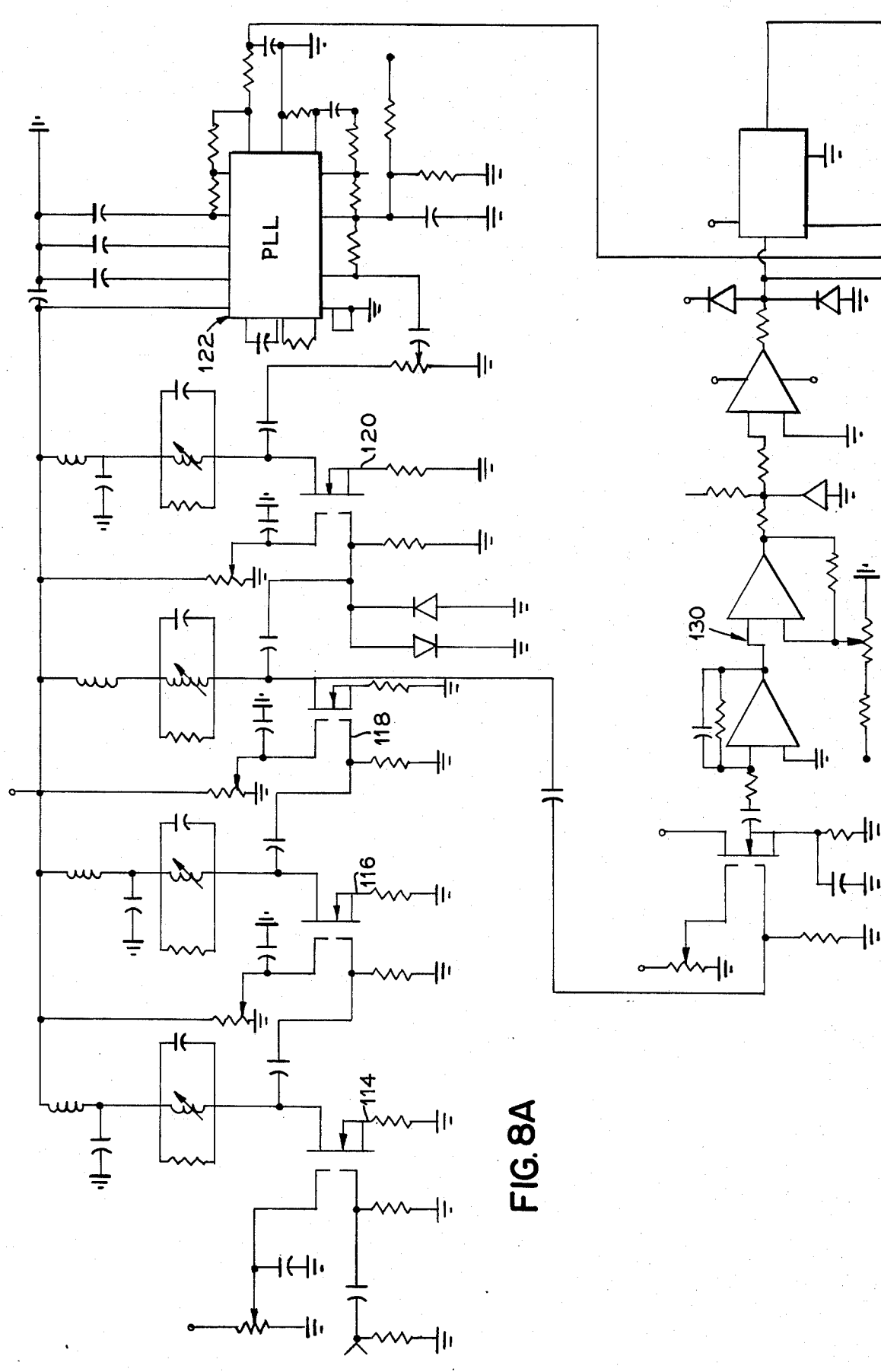
FIGS. 8A and 8B are electrical circuit diagrams showing the signal processor of FIG. 7.
Figure 8B:
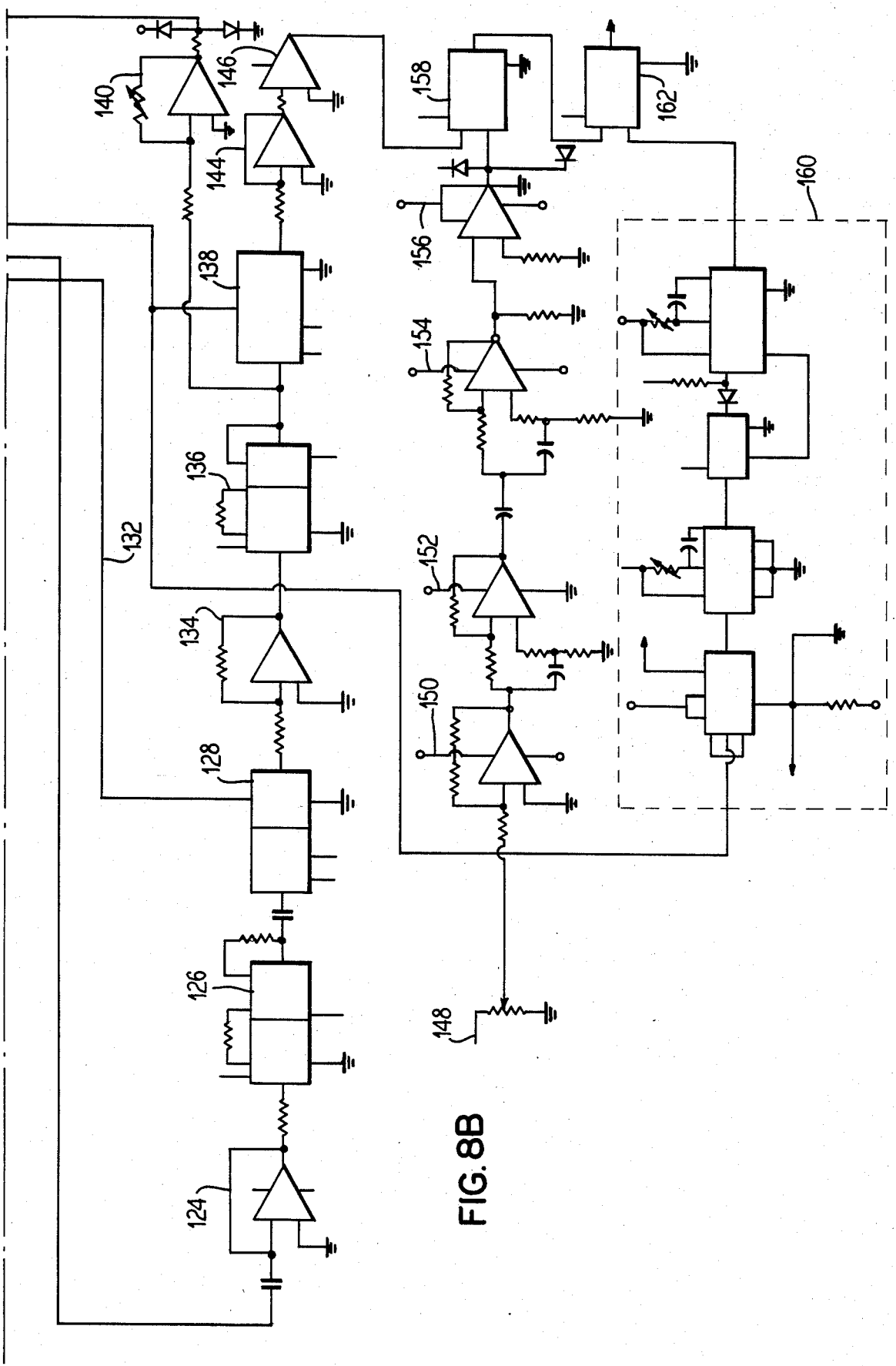

The circuitry for the signal processor 86 is shown in more detail in FIGS. 8A and 8B.

The size counter 88 is shown in FIG. 9 and includes inputs 142 and 160 from the signal processor 86 over which the phase difference signal and the recovered velocity signal are fed. The size counter 88 translates this pulse width into a particle size measurement. The size counter 88, in conjunction with the rest of the signal processing circuitry, distinguishes particle motion due to the acoustic field from motion due to the electric field.

A measure of the duration of the phase difference pulses is accomplished by a 16 bit binary ripple counter 166 that is normally held in the reset condition and is activated by the detection of an RF signal on lead 142. An oscillator 168, such as a 12.416 MHz oscillator, is gated by NAND gate 170 and NOR gate 172 to a clock input 174 of the counter 166 which produces a count that is proportional to the duration of the phase difference pulse. The phase lag count is fed through tri-state buffers 176 and then to the microprocessor 92 over data bus 178. In a preferred embodiment, four such phase lag counts are accumulated and the average is found for increased accuracy. A lead 180 connects the size counter 88 to the charge counter 90.

Figure 10:
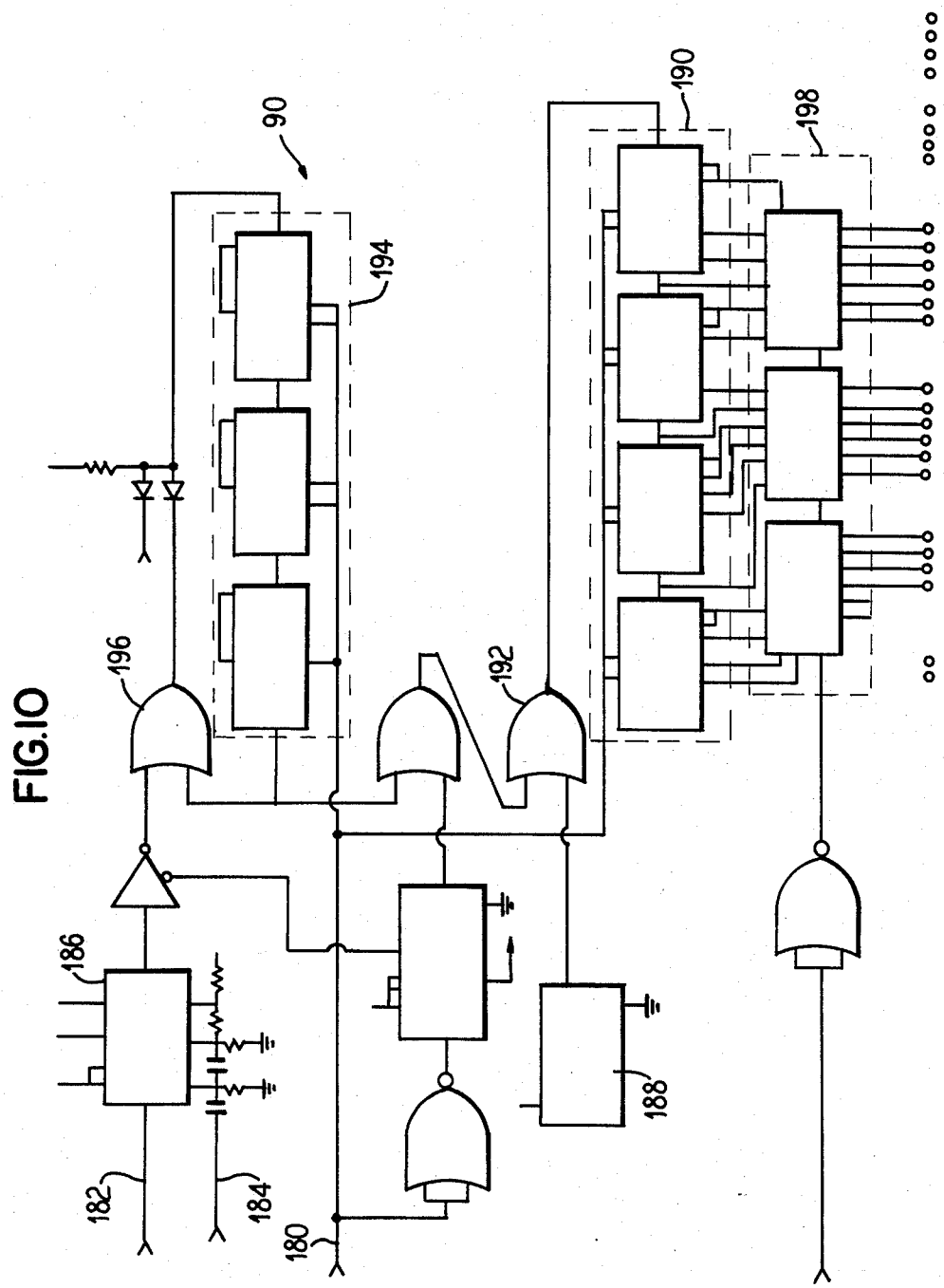
FIG. 10 is an electrical diagram of the charge counter of FIG. 5.

A charged particle moving within the measuring volume 38 will be attracted or repelled by an electric field, resulting in a frequency shift in the RF signal received by the photomultiplier 56. The charge counter 90 shown in FIG. 10 measures this frequency shift from the 2 MHz center frequency so that the number of charges on a particle can be determined.

The 2 MHz RF subcarrier signal is received from the signal processor 86 over lead 184, while leads 180 and 182 carry signals from the size counter 88. The 2 MHz signal is shaped into a square wave by a comparator 186. When a signal is received over lead 180, indicating that a particle is in the measuring volume, the output of a 40 MHz TTL oscillator 188 is gated to a four stage ripple counter 190 by gate 192. At the same time, the RF signal is gated to a three stage counter 194 by gate 196. After 1024 zero crossings of the 2 MHz carrier, the gate 192 is closed. The number resulting on the counter 190 represents the period of the 2 MHz RF subcarrier. The value of the unshifted carrier is subtracted from the resulting number on counter 190 to give a net frequency shift, which represents the particles electric mobility, or charge, when the diameter of the particle is known. Tri-state buffers 198 interface with the microprocessor 92 over data bus 200. Control logic is provided to synchronize data access.

The Software Structure

Appendix A lists software programs used with the present device to control its operation. Portions of the program enable a user to control the operation of the present device to take data, to display the data, to print the data, or to transfer the data to a disk drive system, as well as to plot the aerosol size and charge distributions and to produce three dimensional representations of the charge and size distribution of the sampled aerosol.

In a preferred embodiment the device operates by assigning a plurality of channels to the particle size detection circuitry and, upon determining a particle's size, the size information is placed into one of the channels corresponding to the approximate size of a particle. Thus, recalculation of the size formula is avoided for each particle speeding up the analyzing process.

The present device can be used to detect and analyze in real time up to 100 particles per second. Even faster particle detection rates are possible by keeping the polarity of the voltage pulses constant from one pulse into the next instead of alternating the polarity of the pulses. At higher rates, however, there is a greater likelihood of coincidence errors, caused by more than one particle in the measuring volume 38.

The present device can also be used to determine particle concentrations within an aerosol by dividing the total number of particles counted by the run time and effective sample rate in units of flow.

Accomodation to Particles of Various Sizes

The present device can analyze particles of a predetermined size range as determined by a number of parameters. By varying these parameters, the size range in which the present analyzer will operate can also be varied. For instance, for a particular angle of intersection of the two light beams 26 and 28, the spacing of the interference planes 82 inside the measuring volume 38 is determined. By changing the angle of intersection of the two light beams 26 and 28, the spacing of the interference planes 82 may also be changed. Other parameters which may also be changed to accommodate particles of different size include: the frequency of the acoustic drive, the pulse duration of the electric field, and the residence time of the particles as controlled by the flow rates of the sheath air and the aerosol sample air.

A Dual Range, Dual Chamber Analyzer

Figure 11:
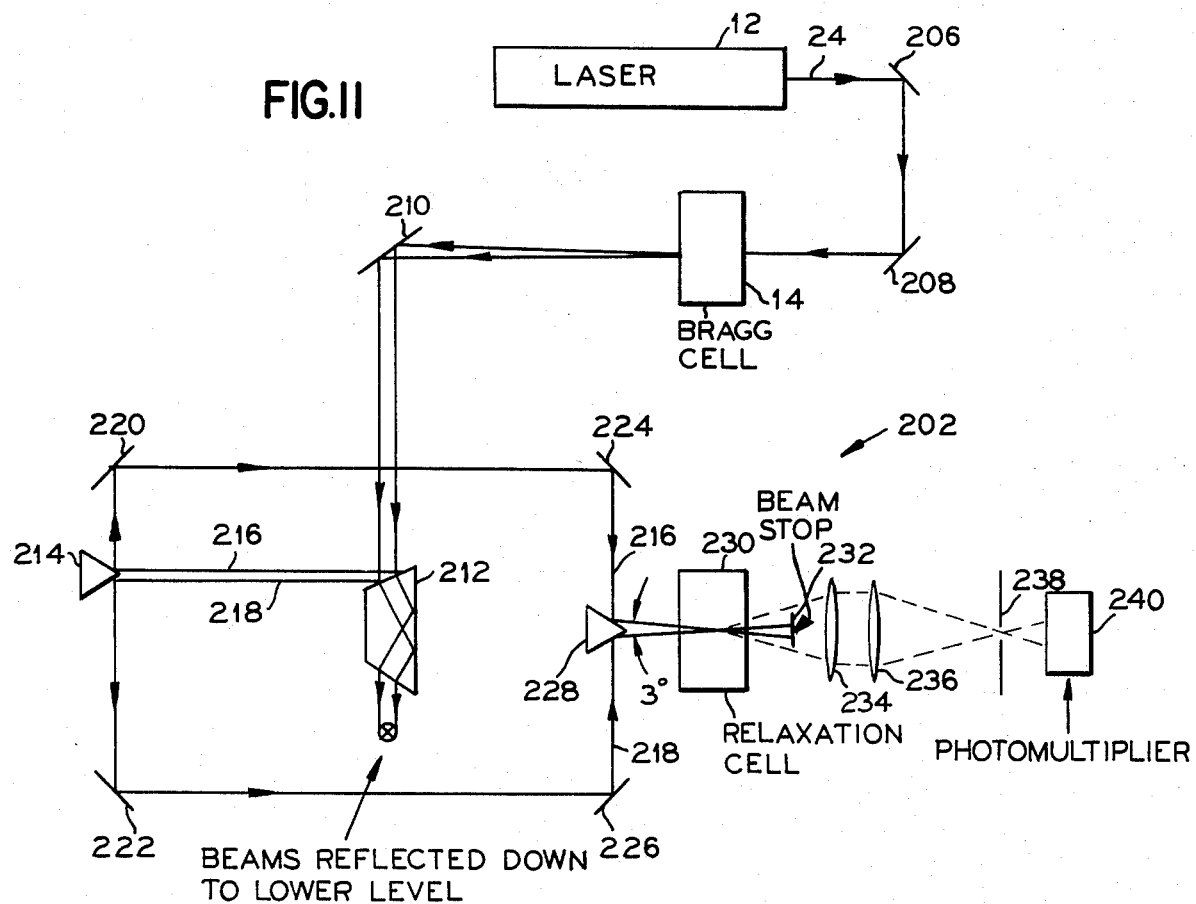
FIG. 11 is a schematic diagram of a large particle measurement portion of an embodiment of the present invention.
Figure 12:
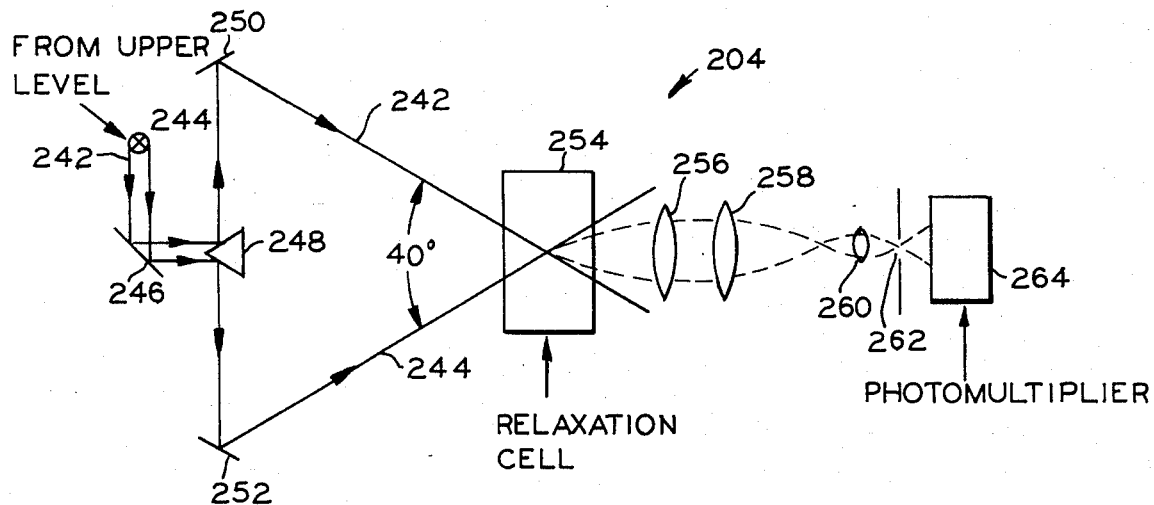
FIG. 12 is a schematic diagram of a small particle measurement portion of the embodiment shown in FIG. 11.

One embodiment of the present device includes the feature of simultaneous dual range particle size analyzation. A first, or large particle, portion 202 of this embodiment is shown in FIG. 11 and a small particle portion 204 is shown in FIG. 12. The first portion 202 includes a monochromatic laser 12 that has a wavelength of 488 nanometers and a power output that is variable from 100 to 800 milowatts. The light beam 24 is reflected by a pair of mirrors 206 and 208 to the acousto-optic modulator 14 which provides a second beam shifted in frequency of 40 MHz. The two beams are then deflected by a mirror 210 into a dove prism beam splitter 212 which produces two pairs of beams, one pair for each particle size range. Other types of beam splitters, such as a standard cube or dielectric beam splitter, are also contemplated for use in the present device.

The first beam pair 216 and 218 of the first, or large particle, portion 202 of the present embodiment are incident on a bi-mirror prism 214, the apex of which is centered midway between the beam pair 216 and 218. Upon reflection, the two beams 216 and 218 separate and travel in opposite directions toward mirrors 220 and 222, respectively. The beams then reflect from a second mirror pair 224 and 226 onto a second bi-mirror prism 228. Upon reflection from the second bi-mirror prism 228 the beams 216 and 218 are focused to intersect within a first relaxation chamber 230.

For measurement of large particles, the angle of intersection of the beams 216 and 218 is small, in the present case being approximately 3°. The small angle of intersection of the two beams 216 and 218 causes the scattered light between the two beams to be too difficult to measure, and therefore a beam stop 232 is placed in the paths of the beams 216 and 218 and the scattered light, which is measured at a larger angle, is focused by lens pair 234 and 236 through an aperture 238 to a first photomultiplier 240.

FIG. 12 shows the second portion, or small particle portion 204, of the present two range embodiment. A second beam pair 242 and 244 is received from the dove prism beam splitter 212 and then reflected by a mirror 246 onto a bi-mirror prism 248, as above. A pair of mirrors 250 and 252 focus the second beam pair 242 and 244 at a relatively large angle, for example 40°, into a second relaxation chamber 254.

The scattered light caused by particles within the measuring volume is collected by a second lens pair 256 and 258 and then is focused through a microscope objective 260 through an aperture 262 to a second photomultiplier 264. Thus, a single light source can drive a two chamber analyzer for analyzing particles in two different size ranges.

Not only must the angle of intersection of the light beams change for different particle sizes but also the frequencies of the acoustic transducers (not shown) within the relaxation chamber 230 and 254 must accommodate different sizes of particles. Thus, the two range, two chamber embodiment also includes dual frequency acoustic drives for driving the acoustic transducers within the relaxation chambers 230 and 254.

FIG. 13 shows an acoustic drive used to drive an acoustic transducer at a frequency of 1 kHz. The one kHz. driver includes a 100 kHz. oscillator 266 which feeds a pair of divide by 10 circuits 268 and 270. The signal is fed through a shaping circuit 272, a buffer 274 and a band pass filter 276 before being connected to a first active transducer in the large particle portion 202. A sinusoidal 1 kHz. acoustic field is thus produced by the first acoustic transducer.

Figure 14:
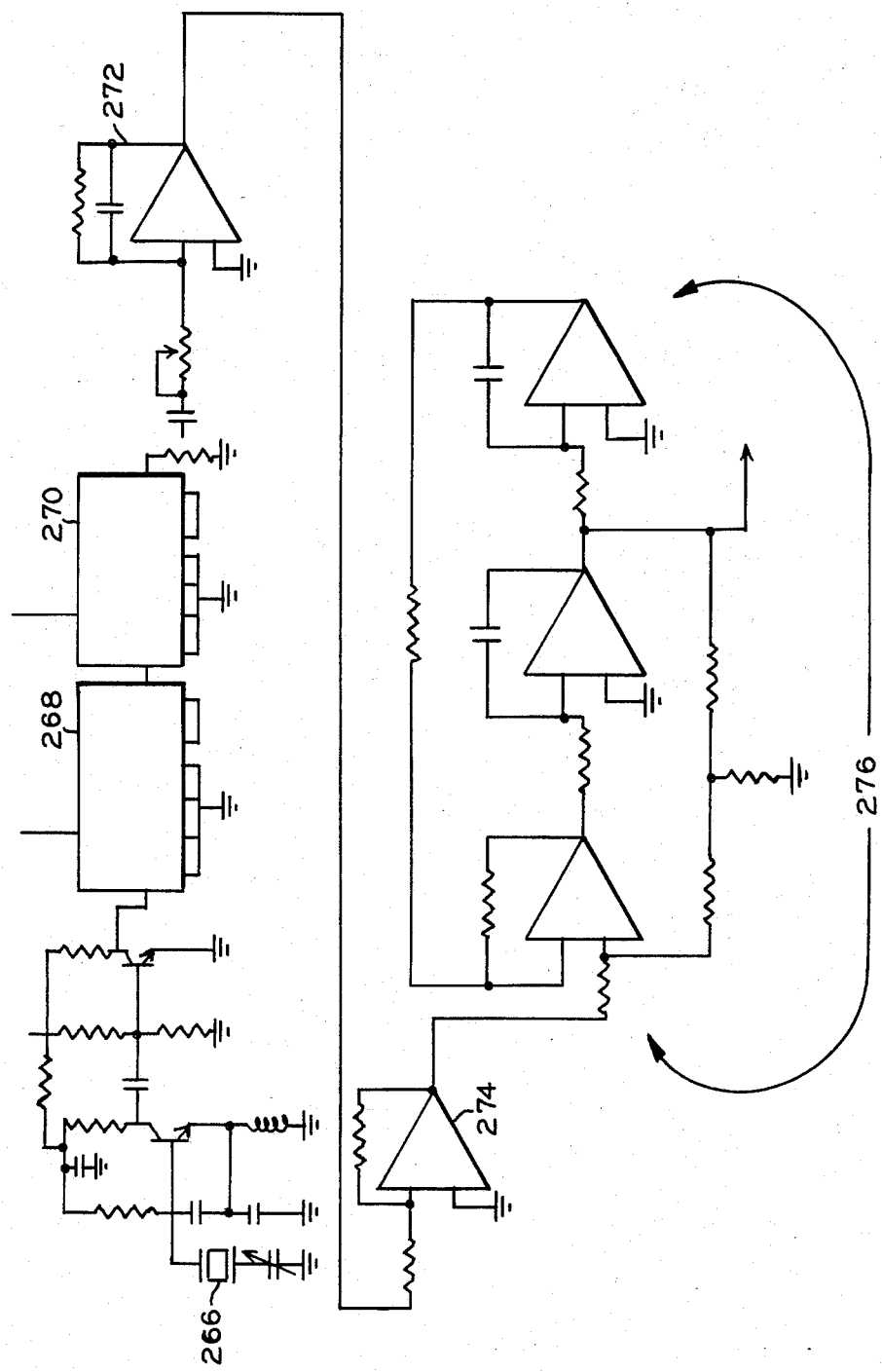
FIG. 14 is an electrical circuit diagram of the acoustic drive shown in FIG. 13.

FIG. 14 is a circuit diagram of the 1 kHz. portion of the circuit of FIG. 13. The oscillator 266 is shown feeding the divide by 10 circuits 268 and 270. The wave shaping circuit 272 in the form of an opamp feeds the buffer 274 which in turn feeds the three stage band pass filter 276. The second acoustic driver shown in FIG. 15 includes a 240 kHz. oscillator 278 which feeds a divide by 10 circuit 280, a wave shaping circuit 282, and then an amplifier 284. This acoustic driver produces a 24 kHz. signal to drive the second active acoustic transducer in the second relaxation chamber 254 for particles of smaller sizes. The circuit diagram of the 24 kHz. driver circuit is shown in FIG. 16.

The above described two particle-size range analyzer operates for particle sizes from 0.2 to 20 micrometers in diameter. The large particle measuring portion 202, shown in FIG. 11 generates interference fringes spaced at approximately 12.0 micrometers and is able to analyze particles in the size range from 2.0 to 20.0 micrometers. The second portion 204 of this embodiment generates interference fringes spaced at approximately 1 micrometer so that particles in the range of 0.2 to 6.0 micrometers in diameter can be analyzed. A wide range of particle sizes thus can be analyzed simultaneously in a device having a dual relaxation chambers and a single laser light source. The laser light beam is split into a first sensing pair for large particles and into a second sensing pair for small particles. Each sensing pair of light beams is focused to form measuring volumes within respective relaxation chambers with respective frequency acoustic fields. It is foreseen to apply this concept to a extend the range of particle sizes which can be analyzed by the present device such as by forming additional chambers. It is also foreseen to vary the sensing parameters in the present device in order to improve sensitivity to a particular particle size or to increase the size range on which the present device operates.

A Dual-Range, Single Chamber Analyzer

Figure 17:
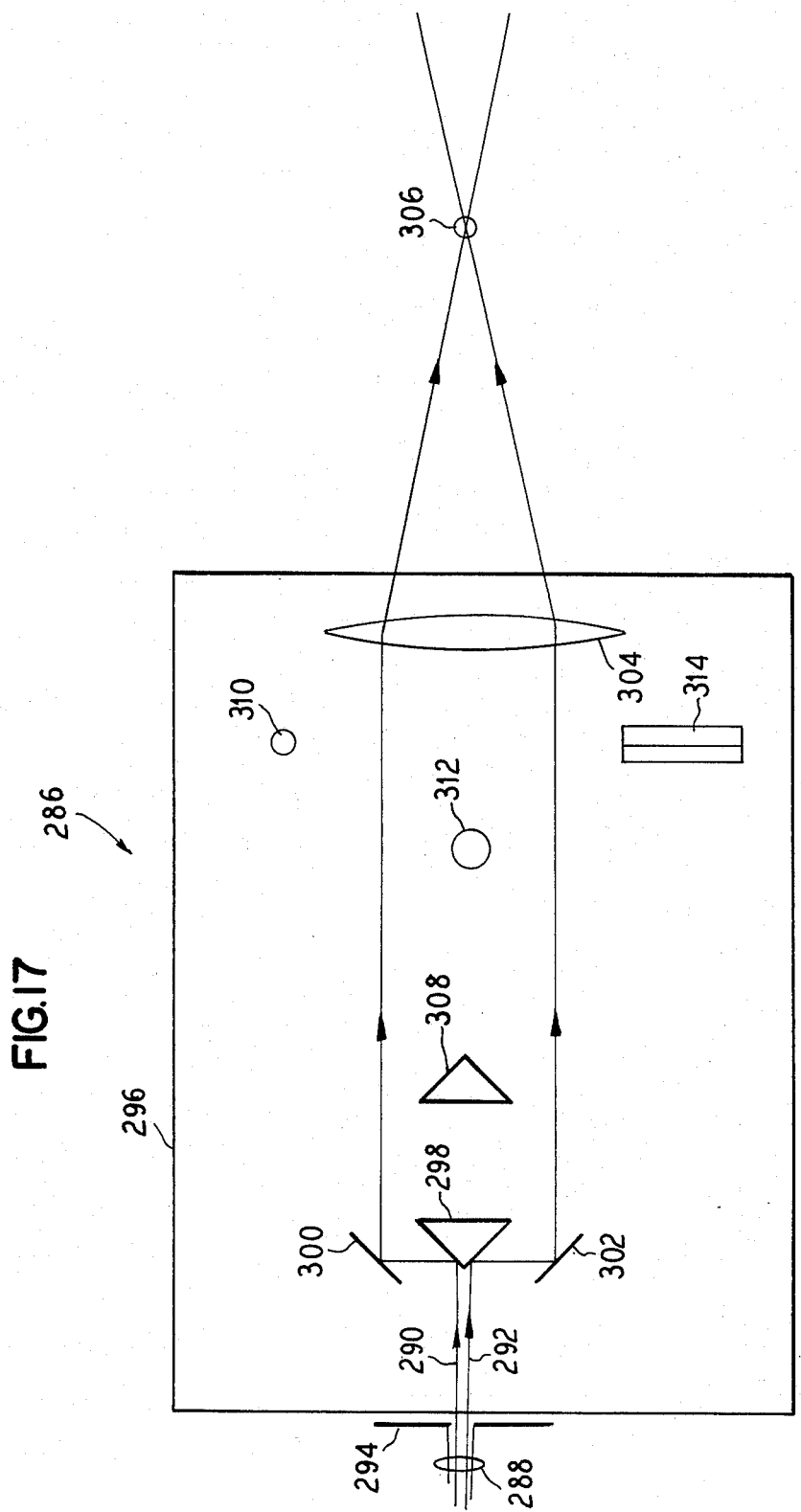
FIG. 17 is a plan view of an optical system for a variable range embodiment of the present invention.

FIG. 17 shows a preferred embodiment of beam focusing apparatus 286. A plurality of diverging light beams 288 are shown which were generated by the acousto-optic modulator 14. All but two of the beams 290 and 292 are blocked by an aperture 294 mounted at the edge of a base plate 296. On the base plate 296 is mounted a mirrored prism 298, as well as mirrors 300 and 302. A lens 304 focuses the light beams 290 and 292 to intersect at a measuring volume 306. An additional mirrored prism 308 is provided on the base plate 296, as are holes 310 and 312 and bearing V-slot 314, the importance of which will become apparent by examining FIG. 18.

Figure 18:
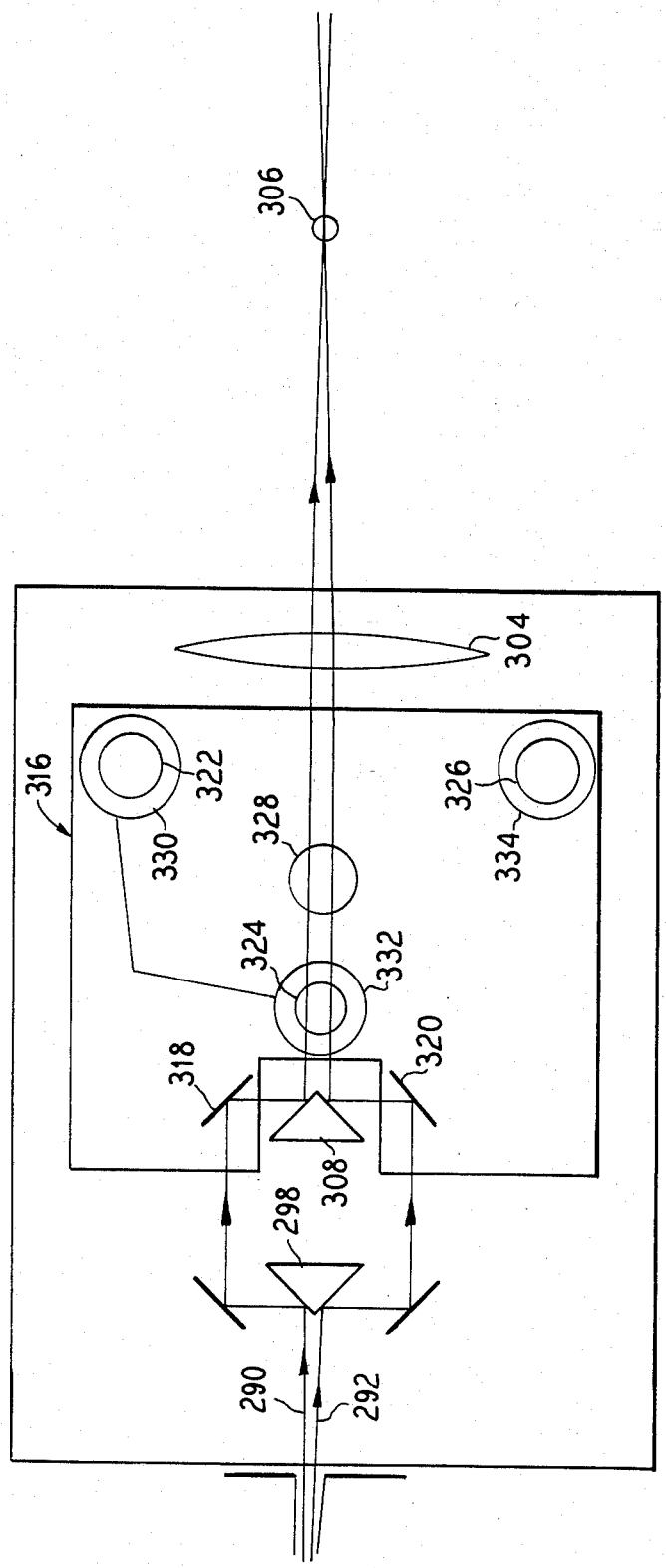
FIG. 18 is a plan view of the optical system of FIG. 17 including a removable optical mount.

FIG. 18 shows the beam focusing apparatus 286 including a removable optical mount 316. The removable optical mount 316 includes two additional mirrors 318 and 320 positioned to change the angle of beam intersection of the two beams 290 and 292. The removable optical mount 316 can be removed and repositioned without changing the location of the measuring volume 306, yet the fringe spacing is changed.

Accurate repositioning of the removable optical mount 316 is achieved by a three point kinamatic support system. Three screws 322, 324 and 326 pass through the plate 316, each with a steel ball bearing (not shown) set on the end. A first bearing sits in the bearing hole 310 in the base plate 296; the second bearing sits in the V-slot 314 in the same base plate 296 for repositioning rotational orientation; and the third bearing sits directly on top of the base plate 296. The removable optical mount 316 is then spring mounted by spring loaded mounting bolt 328 to threaded hole 312 to the base plate 296. The three screws 322, 324 and 326 are used to set the removable amount 316 parallel to the base plate 296 before the mirrors 318 and 320 are initially aligned. Lock nuts 330, 332 and 334, respectively, are then tightened to prevent any motion after this initial alignment.

Thus, by changing the angle of intersection of the two light beams 290 and 292, the particle size range which may be analyzed by the present device is changed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method of determining the charge and aerodynamic size of a particle, comprising the steps of:
   (a) propagating an acoustic field on a directionalized first axis at a given location,
   (b) driving a gaseous carrier stream carrying particles of indeterminate size and charge,
   (c) directing said laden carrier stream into said acoustic field at a directionalized second axis transverse to said first axis to produce a difference between the motion of the particle and the motion of the gaseous carrier stream,
   (d) propagating a directionalized electrical field at the same location as said acoustic field to produce a unidirectional drift velocity on the particle which is a function of the charge and polarity of said particle,
   (e) and monitoring said particle to determine the quantum of said difference and of said unidirectional drift velocity as a measure of its charge and aerodynamic size.

2. A method as claimed in claim 1 wherein step (c) produces a phase difference and wherein step (e) includes the step of determining the quantum of phase difference.

3. A method as claimed in claim 1 wherein step (c) produces an amplitude difference and wherein step (e) includes the step of determining the quantum of said amplitude difference.

4. A method as claimed in claim 1, wherein said acoustic field is sinusoidal.

5. A method as claimed in claim 1, wherein said electric field is propagated by electric pulses of alternating polarity.

6. A method as claimed in claim 1, wherein step e further comprises:

generating an interference pattern of electromagnetic waves, focusing said interference pattern at the location of said acoustic field and said electric field to cause particles moving in said interference pattern to scatter frequency modulated electromagnetic waves, sensing said frequency modulated electromagnetic waves scatterd by said particles, demodulating said sensed frequency modulated waves, comparing said demodulated waves to a reference signal representing said acoustic field, quantifying said difference between the motion of said particle and the motion of said gaseous carrier stream, and quantifying said unidirectional drift velocity of said particle.

7. A method as claimed in claim 6, further comprising the steps of:

storing said quantified motion difference and said quantified drift velocity for each particle in said interference pattern, and plotting said motion difference quantities and said drift velocity quantities for an aeorosol sample.

8. An apparatus for determining the size and charge of a particle in a fluid suspension, comprising:

means forming a chamber, means for directing a stream of fluid in which particles to be measured are entrained into said chamber, an acoustic transducer for generating an acoustic field within said chamber, first and second electrode elements disposed opposite one another for generating an electric field within said chamber, said means forming said chamber having windows for admitting laser beams into said chamber and for enabling light scattered by the particles to exit said chamber, and laser actuated detecting means for projecting laser beams through said windows and for detecting the scattered light radiations which are a function of particle size and charge.

9. An apparatus as claimed in claim 8, further comprising:

means for adjustably mounting said acoustic transducer relative to said stream of fluid.

10. An apparatus as claimed in claim 8, further comprising:

means connected to said acoustic transducer for causing said transducer to generate a sinusoidal acoustic field.

11. An apparatus as claimed in claim 8, further comprising:

means connected to said first and second electrode elements for causing said first and second electrode elements to generate a pulsed electrical field.

12. An apparatus as claimed in claim 11, wherein said means connected to said first and second electrode elements causes said first and second electrode elements to generate an alternating pulsed electrical field.

13. An apparatus as claimed in claim 8, further comprising:

a second acoustic transducer mounted to monitor said acoustic field within said chamber.

14. An apparatus as claimed in claim 13, wherein said first and second electrode elements are mounted across the face of respective ones of said first and second acoustic transducers.

15. An apparatus as claimed in claim 8, further comprising:

means for determining the size of the particle from said detected scattered light radiations, and means for determining the charge of the particle from said detected scattered light radiations.

16. An apparatus as claimed in claim 15, further comprising:

means for plotting the size and charge distribution of a plurality of particles in fluid suspension.

17. An apparatus as claimed in claim 15, wherein:

said means for detecting scattered light radiations includes a photomultiplier tube, and said means for determining the size of the particle and said means for determining the charge of the particle includes a mixer connected to an output of said photomultiplier tube, a demodulator connected to process signals from said mixer, and a comparator connected to an output of said demodulator, to compare said processed signals to a reference signal.

18. An apparatus for determining the size and charge of a plurality of particles in an aerosol sample, comprising:

a laser Doppler velocimeter including an acousto-optic modulator connected to produce a diverging beam pair, a beam focusing apparatus mounted to focus said diverging beam pairs to form a measuring volume of interference planes, a relaxation chamber into which said diverging beam pair is focused, means for establishing an air flow of said aerosol sample through said relaxation chamber substantially parallel to said interference planes, an active acoustic transducer connected to generate an acoustic field within said relaxation chamber transverse to said air flow, a passive acoustic transducer mounted to monitor said acoustic field within said relaxation chamber to produce a reference signal, first and second electrode elements mounted across respective ones of said active and passive acoustic transducers and connected to generate a pulsed electric field within said relaxation chamber simultaneously with said acoustic field, whereby particles in said aerosol sample within said measuring volume are moved by said acoustic field and said electric field thereby scattering light from said interference planes, means for focusing said scattered light from the motion of the particles, a photodetector mounted to sense said focused scattered light and thereby produce an electrical signal, a signal processor connected to receive said electrical signal from said photodetector and connected to said passive acoustic transducer to receive said reference signal, a size counter connected to said signal processor to generate particle size data, a charge counter connected to said signal processor to generate particle charge data, and program controlled means for accumulating said particle size data and said particle charge data.

* * * * *